US011464646B2

(12) United States Patent
Thibodeau

(10) Patent No.: US 11,464,646 B2
(45) Date of Patent: *Oct. 11, 2022

(54) EXPANDABLE SPINAL IMPLANT APPARATUS AND METHOD OF USE

(71) Applicant: Stryker European Operations Holdings, LLC, Wilmington, DE (US)

(72) Inventor: Lee L. Thibodeau, Cumberland, ME (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 442 days.

This patent is subject to a terminal disclaimer.

(21) Appl. No.: 16/535,420

(22) Filed: Aug. 8, 2019

(65) Prior Publication Data

US 2019/0374345 A1 Dec. 12, 2019

Related U.S. Application Data

(63) Continuation of application No. 15/429,346, filed on Feb. 10, 2017, now Pat. No. 10,413,419, which is a
(Continued)

(51) Int. Cl.
*A61F 2/44* (2006.01)
*A61F 2/46* (2006.01)
(Continued)

(52) U.S. Cl.
CPC .......... *A61F 2/442* (2013.01); *A61F 2/30771* (2013.01); *A61F 2/44* (2013.01);
(Continued)

(58) Field of Classification Search
CPC ...... A61F 2/4455; A61F 2/446; A61F 2/4465; A61F 2/447; A61F 2/4611
See application file for complete search history.

(56) References Cited

U.S. PATENT DOCUMENTS 4,863,476 A 9/1989 Shepperd
5,390,683 A 2/1995 Pisharodi
(Continued)

OTHER PUBLICATIONS

Anulex Brochure "X-Ciose Tissue Repair System," 2007, 2pp.
(Continued)

*Primary Examiner* — Ellen C Hammond
(74) *Attorney, Agent, or Firm* — Lerner, David, Littenberg, Krumholz & Mentlik, LLP

(57) ABSTRACT

A spinal implant apparatus that is an expandable spacer including features to minimize or eliminate spacer cant or offset during and after completing the expansion process. The spacer includes a top component, a base component in engagement with the top component, and an expansion mechanism arranged to change the top component's position with respect to the base component. The mechanism for causing expansion may be a screw, a cam, a wedge or other form of distracting device. In one embodiment, the expandable spacer includes a base component with a set of towers and a top component with a set of corresponding silos, where the towers and silos are configured to minimize or eliminate tilt of the top component as it extends upwardly from the base component.

13 Claims, 12 Drawing Sheets

Related U.S. Application Data continuation of application No. 14/700,554, filed on Apr. 30, 2015, now Pat. No. 9,603,715, which is a continuation of application No. 12/774,429, filed on May 5, 2010, now Pat. No. 9,050,194.

(60) Provisional application No. 61/175,918, filed on May 6, 2009.

(51) Int. Cl.
  *A61F 2/30* (2006.01)
  *A61F 2/28* (2006.01)

(52) U.S. Cl.
  CPC .......... *A61F 2/4455* (2013.01); *A61F 2/4465* (2013.01); *A61F 2/4611* (2013.01); *A61F 2002/2835* (2013.01); *A61F 2002/3037* (2013.01); *A61F 2002/3052* (2013.01); *A61F 2002/30133* (2013.01); *A61F 2002/30281* (2013.01); *A61F 2002/30354* (2013.01); *A61F 2002/30367* (2013.01); *A61F 2002/30372* (2013.01); *A61F 2002/30387* (2013.01); *A61F 2002/30507* (2013.01); *A61F 2002/30518* (2013.01); *A61F 2002/30535* (2013.01); *A61F 2002/30556* (2013.01); *A61F 2002/30579* (2013.01); *A61F 2002/30593* (2013.01); *A61F 2002/30604* (2013.01); *A61F 2002/30774* (2013.01); *A61F 2002/30782* (2013.01); *A61F 2220/0025* (2013.01); *A61F 2220/0033* (2013.01); *A61F 2230/0015* (2013.01); *A61F 2230/0086* (2013.01); *A61F 2250/0009* (2013.01)

(56) References Cited

U.S. PATENT DOCUMENTS

| | | |
|---|---|---|
| 5,665,122 A | 9/1997 | Kambin |
| 5,702,455 A | 12/1997 | Saggar |
| 5,782,832 A | 7/1998 | Larsen et al. |
| 6,083,225 A | 7/2000 | Winslow et al. |
| 6,117,174 A | 9/2000 | Nolan |
| 6,129,763 A | 10/2000 | Chauvin et al. |
| 6,176,882 B1 | 1/2001 | Biedermann et al. |
| 6,190,414 B1 | 2/2001 | Young et al. |
| 6,245,075 B1 | 6/2001 | Betz et al. |
| 6,302,914 B1 | 10/2001 | Michelson |
| 6,443,989 B1 | 9/2002 | Jackson |
| 6,447,544 B1 | 9/2002 | Michelson |
| 6,517,544 B1 | 2/2003 | Michelson |
| 6,520,967 B1 | 2/2003 | Cauthen |
| 6,524,341 B2 | 2/2003 | Lang et al. |
| 6,562,074 B2 | 5/2003 | Gerbec et al. |
| 6,592,625 B2 | 7/2003 | Cauthen |
| 6,706,070 B1 | 3/2004 | Wagner et al. |
| 6,770,074 B2 | 8/2004 | Michelson |
| 6,773,460 B2 | 8/2004 | Jackson |
| 6,814,737 B2 | 11/2004 | Cauthen |
| 6,821,276 B2 | 11/2004 | Lambrecht et al. |
| 6,830,589 B2 | 12/2004 | Erickson |
| 6,852,129 B2 | 2/2005 | Gerbec et al. |
| 6,883,520 B2 | 4/2005 | Lambrecht et al. |
| 6,905,512 B2 | 6/2005 | Paes et al. |
| 6,936,072 B2 | 8/2005 | Lambrecht et al. |
| 6,984,247 B2 | 1/2006 | Cauthen |
| 6,997,956 B2 | 2/2006 | Cauthen |
| 7,004,970 B2 | 2/2006 | Cauthen, III et al. |
| 7,033,395 B2 | 4/2006 | Cauthen |
| 7,094,257 B2 | 8/2006 | Mujwid et al. |
| 7,094,258 B2 | 8/2006 | Lambrecht et al. |
| 7,118,579 B2 | 10/2006 | Michelson |
| 7,124,761 B2 | 10/2006 | Lambrecht et al. |
| 7,128,760 B2 | 10/2006 | Michelson |
| 7,144,397 B2 | 12/2006 | Lambrecht et al. |
| 7,189,235 B2 | 3/2007 | Cauthen |
| 7,198,047 B2 | 4/2007 | Lambrecht et al. |
| 7,211,112 B2 | 5/2007 | Baynham et al. |
| 7,220,281 B2 | 5/2007 | Lambrecht et al. |
| 7,258,700 B2 | 8/2007 | Lambrecht et al. |
| 7,691,147 B2 | 4/2010 | Gutlin et al. |
| 7,708,779 B2 | 5/2010 | Edie et al. |
| 7,744,649 B2 | 6/2010 | Moore |
| 7,753,958 B2 | 7/2010 | Gordon et al. |
| 7,799,081 B2 | 9/2010 | McKinley |
| 7,819,920 B2 | 10/2010 | Assaker |
| 7,850,733 B2 | 12/2010 | Baynham et al. |
| 8,105,382 B2 | 1/2012 | Olmos et al. |
| 8,118,870 B2 | 2/2012 | Gordon et al. |
| 8,118,871 B2 | 2/2012 | Gordon et al. |
| 8,216,317 B2 | 7/2012 | Thibodeau |
| 8,425,559 B2 | 4/2013 | Tebbe et al. |
| 8,435,296 B2 | 5/2013 | Kadaba et al. |
| 8,556,979 B2 | 10/2013 | Glerum et al. |
| 2002/0045944 A1 | 4/2002 | Muhanna et al. |
| 2002/0138146 A1* | 9/2002 | Jackson ................ A61F 2/4455 623/17.15 |
| 2003/0018389 A1 | 1/2003 | Castro et al. |
| 2003/0065396 A1 | 4/2003 | Michelson |
| 2003/0135275 A1 | 7/2003 | Garcia et al. |
| 2003/0199874 A1 | 10/2003 | Michelson |
| 2004/0049271 A1 | 3/2004 | Biedermann et al. |
| 2004/0054412 A1 | 3/2004 | Gerbec et al. |
| 2004/0068259 A1 | 4/2004 | Michelson |
| 2004/0127994 A1 | 7/2004 | Kast et al. |
| 2004/0153156 A1 | 8/2004 | Cohen et al. |
| 2004/0153160 A1 | 8/2004 | Carrasco |
| 2004/0162618 A1 | 8/2004 | Mujwid et al. |
| 2004/0167536 A1 | 8/2004 | Errico et al. |
| 2004/0236331 A1 | 11/2004 | Michelson |
| 2004/0254643 A1 | 12/2004 | Jackson |
| 2005/0021041 A1 | 1/2005 | Michelson |
| 2005/0149197 A1 | 7/2005 | Cauthen |
| 2005/0165398 A1 | 7/2005 | Reiley |
| 2005/0171541 A1 | 8/2005 | Boehm et al. |
| 2005/0203625 A1 | 9/2005 | Boehm et al. |
| 2005/0209697 A1 | 9/2005 | Paponneau et al. |
| 2005/0216085 A1 | 9/2005 | Michelson |
| 2005/0278026 A1 | 12/2005 | Gordon et al. |
| 2006/0004450 A1 | 1/2006 | McKay |
| 2006/0058876 A1 | 3/2006 | McKinley |
| 2006/0084994 A1 | 4/2006 | Atkinson et al. |
| 2006/0089719 A1 | 4/2006 | Trieu |
| 2006/0100711 A1 | 5/2006 | Cauthen |
| 2006/0129156 A1 | 6/2006 | Cauthen et al. |
| 2006/0129245 A1 | 6/2006 | Cauthen |
| 2006/0142864 A1 | 6/2006 | Cauthen |
| 2006/0149385 A1 | 7/2006 | McKay |
| 2006/0161258 A1 | 7/2006 | Cauthen |
| 2006/0167553 A1 | 7/2006 | Cauthen et al. |
| 2006/0173545 A1 | 8/2006 | Cauthen et al. |
| 2006/0190083 A1 | 8/2006 | Amin et al. |
| 2006/0190085 A1 | 8/2006 | Cauthen |
| 2006/0200244 A1 | 9/2006 | Assaker |
| 2006/0229729 A1 | 10/2006 | Gordon et al. |
| 2006/0241761 A1 | 10/2006 | Gately |
| 2006/0241770 A1 | 10/2006 | Rhoda et al. |
| 2006/0241773 A1 | 10/2006 | Cauthen |
| 2006/0241774 A1 | 10/2006 | Attali et al. |
| 2006/0282167 A1 | 12/2006 | Lambrecht et al. |
| 2007/0093897 A1 | 4/2007 | Gerbec et al. |
| 2007/0093906 A1 | 4/2007 | Hudgins et al. |
| 2007/0123989 A1 | 5/2007 | Gfeller et al. |
| 2007/0156243 A1 | 7/2007 | Errico et al. |
| 2007/0162138 A1 | 7/2007 | Heinz |
| 2007/0191954 A1 | 8/2007 | Hansell et al. |
| 2007/0208343 A1 | 9/2007 | Magerl et al. |
| 2007/0213737 A1 | 9/2007 | Schermerhorn et al. |
| 2007/0213826 A1 | 9/2007 | Smith et al. |
| 2007/0225808 A1 | 9/2007 | Warnick |
| 2007/0225814 A1 | 9/2007 | Atkinson et al. |
| 2007/0225815 A1 | 9/2007 | Keith et al. |
| 2007/0225816 A1 | 9/2007 | Keith et al. |

(56) References Cited

U.S. PATENT DOCUMENTS

| | | |
|---|---|---|
| 2007/0233257 A1 | 10/2007 | Keith et al. |
| 2007/0239277 A1 | 10/2007 | Beger et al. |
| 2007/0239280 A1 | 10/2007 | Keith et al. |
| 2007/0255408 A1 | 11/2007 | Castleman et al. |
| 2007/0255413 A1 | 11/2007 | Edie et al. |
| 2007/0255415 A1 | 11/2007 | Edie et al. |
| 2007/0270968 A1 | 11/2007 | Baynham et al. |
| 2008/0009880 A1 | 1/2008 | Warnick et al. |
| 2008/0091211 A1 | 4/2008 | Gately |
| 2008/0109005 A1 | 5/2008 | Trudeau et al. |
| 2008/0140207 A1* | 6/2008 | Olmos ............... A61B 17/025 623/17.16 |
| 2008/0183204 A1 | 7/2008 | Greenhalgh et al. |
| 2008/0221694 A1 | 9/2008 | Warnick et al. |
| 2008/0243254 A1 | 10/2008 | Butler |
| 2009/0112325 A1 | 4/2009 | Refai et al. |
| 2009/0143861 A1 | 6/2009 | Errico et al. |
| 2009/0190083 A1 | 7/2009 | Lee et al. |
| 2009/0216331 A1 | 8/2009 | Grotz et al. |
| 2009/0234364 A1 | 9/2009 | Crook |
| 2009/0248092 A1 | 10/2009 | Bellas et al. |
| 2009/0265008 A1 | 10/2009 | Thibodeau |
| 2009/0292361 A1 | 11/2009 | Lopez |
| 2010/0145455 A1 | 6/2010 | Simpson et al. |
| 2010/0174371 A9 | 7/2010 | Errico et al. |
| 2010/0185291 A1 | 7/2010 | Jimenez et al. |
| 2010/0211176 A1* | 8/2010 | Greenhalgh ............ A61F 2/447 623/17.15 |
| 2010/0222884 A1 | 9/2010 | Greenhalgh |
| 2010/0256759 A1 | 10/2010 | Hansell et al. |
| 2010/0280622 A1 | 11/2010 | McKinley |
| 2010/0292796 A1 | 11/2010 | Greenhalgh et al. |
| 2011/0035011 A1 | 2/2011 | Cain |
| 2011/0202135 A1 | 8/2011 | Baek et al. |

OTHER PUBLICATIONS

Anulex brochure, "Inclose Surgical Mesh System," 2007, 2pp.
Gorensek, M. et al., "Clinical Investigation of the Intrinsic Therapeutics Barricaid, a Novel Devise for Closing Defects in the Anulus," presented at the North American Spine Society; Sep. 27-30, 2006, 2pp.
Humphries, S. Craig, "Clinical Evaluation and Treatment Options for Herniated Lumbar Disc," American Family Physician, Feb. 1, 1999, 10pp.
Intrinsic Therapeutics brochure, "The Science of Disc Repair," undated, 2pp.
PCT International Search Report and Written Opinion, PCT Application No. PCT/US2010/033760, dated Aug. 19, 2010, 9 pp.

\* cited by examiner

EXPANDABLE SPINAL IMPLANT APPARATUS AND METHOD OF USE

CROSS-REFERENCE TO RELATED APPLICATIONS

The present application is a continuation of U.S. patent application Ser. No. 15/429,346, filed Feb. 10, 2017, which is a continuation of U.S. patent application Ser. No. 14/700,554, filed Apr. 30, 2015 and issued as U.S. Pat. No. 9,603,715, which is a continuation of U.S. patent application Ser. No. 12/774,429, filed May 5, 2010 and issued as U.S. Pat. No. 9,050,194, which relates to, and claims priority in, U.S. Provisional Patent Application Ser. No. 61/175,918, entitled "EXPANDABLE SPINAL IMPLANT APPARATUS" filed May 6, 2009 by the same inventor. The contents of all of these applications are incorporated herein by reference.

BACKGROUND OF THE INVENTION

1. Field of the Invention

The present invention relates to an expandable spinal implant apparatus and a method of using the apparatus to treat a spine disorder. More particularly, the present invention relates to an intervertebral spacer arranged for expansion of one or more dimensions of the spacer without canting, tilting, or slipping, and methods of using the expandable spacer.

2. Description of the Prior Art

Back pain can be caused by anyone of several problems that affect the vertebral discs of the spine. These problems include, for example, degeneration, bulging, herniation, thinning of a disc, or abnormal movement, and the pain that is experienced generally is attributable to friction or pressure that inevitably occurs when one adjacent vertebra exerts uneven pressure, or when both adjacent vertebrae exert such pressure, on the disc. Back pain may also be attributed to neural element injury.

Whenever an individual suffers from a disc problem, a typical remedy is to perform interbody, intervertebral, cervical, thoracic or lumbar fusion (all generically referred to herein as IF) surgery on the patient for the purpose of fusing the two vertebrae that flank the defective disc to form a single, solid bone mass. Existing IF techniques generally involve removing the offending disc from the patient, adding bone graft material into the interbody space between the flanking vertebrae, and also inserting a spinal implant device into that space to hold the graft material in place and to support the flanking vertebrae while solid bone mass forms.

Existing IF techniques fail to enable fine positioning or stable expansion of an implant device with respect to the vertebrae. A brief discussion of the basic anatomy of the human spine, and specifically, the lumbar vertebrae of the spine, will help better illustrate this limitation. FIG. 1 shows a representation of a human vertebral disc 310, as it is arranged between a superior vertebra 320 and an inferior vertebra 330, in a partial representation of the lumbar region of a human spine. Specifically, the disc 310 is positioned between bottom surface 321 of the superior vertebra 320 and top surface 331 of the inferior vertebra 330. FIG. 2 shows a representation of the top surface 331 of the inferior vertebra 330. The inferior vertebra 330 includes a vertebral body 332 formed by a cortical rim 333, which is a dense, hard shell that is formed by compact bone, and an end plate portion 334, which is formed by much softer and less compact end plate material.

Referring to FIG. 3, existing IF procedures, including those associated with the lumbar region, involve positioning one or two spinal implant devices (an exemplary existing spinal implant device is shown as element 350 in FIG. 3) substantially centered on the end plate portion 334 of the inferior vertebra 330 and the bottom surface 321 of the end plate portion of the superior vertebra 320. Positioning the device in this way does not promote lordosis. Further, in this position, the device 350 tends to depress upon, or even become embedded in, the end plate portion 334 of the inferior vertebra 330 and/or the opposing end plate portion 324 of the superior vertebra 320. This settling of the implant device is referred to as subsidence. When this subsidence occurs, the vertebrae-supporting properties of the device 350 are reduced or eliminated. The result may be loss of intervertebral space height and/or less than desirable coronal and/or sagittal alignment of the spine.

Existing IF procedures are further limited in other ways. During IF surgery, the surgeon must navigate the spinal implant device through a region that is densely packed with neural elements, muscle, ligaments, tendons and bone to access the top surface 331 of the inferior vertebra 330. In existing IF techniques, this requires extensive cutting and/or manipulation of this region, which can extend patient recovery time and subject the patient to other side effects, such as, for example, inflammation, which can be discomforting. Worse, in some patients, the patient must be entered in two or three of three possible body areas (i.e., the patient's posterior region in a posterior interbody fusion technique, the patient's anterior region in an anterior interbody fusion technique, laterally in a lateral interbody fusion technique and/or the patient's transforaminal region in a transforaminal interbody fusion technique) for the purpose of positioning the spinal implant device. It is also to be noted that existing IF techniques are substantially invasive and can be difficult to perform.

One aspect of the limitation of the existing tools used in the IF process relates to the design of the spacer. In some IF procedures, locating the spacer in the position of interest cannot be done by hand alone. Instead, a tool is required to push the spacer to the position of interest, particularly when promoting lordosis is the goal. Present spacers are configured so that the interface with the positioning tool occurs only on the primary longitudinal axis, one of the orthogonal axes, of the spacer. For example, the spacers are rectangular and include a port that is centrally aligned with the primary longitudinal axis of the spacer used to releasably receive the positioning tool therein.

Some spacers include a mechanism for changing the dimensions of the spacer, such as the height dimension. The mechanism permits dimension change after the spacer has been placed at or near the location of interest. The ability to change the height dimension of the spacer improves the chance of achieving desired intervertebral space height as well as coronal and sagittal balance. The present mechanisms may not produce uniform expansion of the spacer. As a result, the spacer may get caught on itself along one side, in a corner, etc., and will end up with a non-uniform height. The spacer is less effective than desired in such a canted state. It can cause pain for the patient and extend the recovery period, possibly with less than complete fusion established.

Another problem with existing expansion mechanisms relates to spacer rocking. That is, for a two-piece spacer in which one part extends from a base piece, the tolerances between the two pieces may be significant enough that the extension piece will rock or pivot on the base piece when in an extended position. This, too, produces a spacer of non-uniform height. The spacer is less effective in producing the desired intervertebral space height and/or coronal/sagittal alignment.

What is needed therefore is an expandable spinal implant apparatus configured to ensure uniform expansion with minimal or no rocking, canting, tilting, or slipping during and after the expansion process. Such an apparatus would decrease patient risk, speed recovery and substantially improve success rates in terms of restoration of normal spinal confirmation (i.e., intervertebral space height as well as coronal and sagittal alignment) and neurological decompression.

BRIEF SUMMARY OF THE INVENTION

It is an object of the present invention to provide an apparatus for treating a patient in need of IF surgery. The present apparatus is an expandable spacer including a top component, a base component in engagement with the top component, and an expansion mechanism arranged to change the top component's position with respect to the base component or vice versa, which results in a change in the size, dimension, and/or shape of the spacer. The top and base components remain in engagement with each other throughout and after the position changing process.

When in position, the top component of the spacer is in contact with the bottom surface of the end plate portion of the superior vertebra, and the base component is in contact with the top surface of the inferior vertebra. The expandable spacer is arranged such that the top component's position may be changed with respect to the base component, or vice versa. The base component and the top component include configurations to keep the two components in substantial contact and alignment with one another throughout the dimension changing process. The two components remain in engagement with one another, either along some or all of their respective perimeters and/or within their interior regions, during the dimension change. This arrangement eliminates the possibility of spacer cant during expansion and when in an expanded state.

The spacer of the present invention includes a configuration that permits the surgeon to expand at least one of its dimensions subsequent to placement at the selected position of interest. While referred to herein as a mechanism to expand a dimension or change the position of the components, it is to be understood that the mechanism causes a change of size, dimension and/or shape of the spacer. The expansion mechanism can be a screw, wedge, cam or any other type of distracting device capable of causing movement of one component of the spacer with respect to another component of the spacer. This is referred to as the position changing process.

Three embodiments of the expandable spacer with configurations designed to increase the engagement of their contacting surfaces in order to minimize or eliminate slipping, tilting, and/or canting during and after the position changing process are disclosed herein. The interfaces and/or surfaces of either or both of the top component and the base component (both external and internal) may be smooth, textured, ribbed, sawtoothed or otherwise modified to optimize the frictional engagement between the components.

The expandable spacer of the present invention may include interior spaces therethrough which promote bone packing and/or bone growth.

In addition, at least a portion of one or more of the exterior surfaces of the top and/or base component may be modified to optimize frictional engagement with the vertebrae between which the spacer is positioned. The spacer may be configured so that it has a higher frictional engagement at the one end. For example, the front end may have a higher frictional engagement and engage tightly with the vertebral end plate whereas the back end of the spacer may have a lower frictional engagement with the vertebral end plate. This configuration enables a desirable type of sliding or positioning of the spacer during insertion.

The expandable spacer may also include one or more off-axis positioning interface sites and/or one or more on-axis positioning interface sites. For purposes of description of the present invention, "off-axis" means a steerage, directional and/or expansion contact location that is anywhere part of the spacer except at a location that is aligned with the primary longitudinal axis of the spacer. An off-axis location may include any non-orthogonal locations as well as orthogonal locations except for the primary longitudinal axis (on axis). The contact sites are arranged for releasable interfacing with a steering and/or expansion tool and enable fine and minimally invasive manipulation within the patient for positioning the spacer at the desirable location.

The spacer includes, for the ease of description, a generally rectangular body shape with one or more curved surfaces, but is not limited thereto. In one or more embodiments it may include one or more chamfered corners of the rectangular shape suitable for including at such corners an off-axis positioning interface, such as a port arranged to allow releasable insertion of a tool insert. For an expandable spacer of the present invention including such off-axis interface port, one or more of the one or more chamfered corners may include a nodule or pin that may be releasably joined to a tool interface. The off-axis version of the spacer is thus configured to enable its steerage from a starting location to the desirable location at more than just straight-line movements using a positioning tool of interest. Such a spacer may be moved at 30°, 45°, or any other angles of interest including orthogonal angles other than on the primary longitudinal axis of the spacer.

The present invention also encompasses a method of inserting, positioning, and expanding the expandable spacer in the intervertebral disc space between two adjacent vertebrae, including the steps of providing an expandable spacer including a top component, a base component in engagement with the top component, and an expansion mechanism arranged to change the top component's position with respect to the base component. The spacer may include one or more off-axis positioning interface sites and/or one or more on-axis positioning sites, the on-axis interface being coincident with or parallel to the longitudinal axis of the spacer, and the off-axis interface being angled with respect to the longitudinal axis. The method further includes the steps of inserting the spacer at least partially into the intervertebral disc space.

The method may further include the steps of engaging a tool to any off-axis or on-axis interface sites of the spacer, and inserting the spacer further into the intervertebral disc space by moving the tool substantially along the insertion direction. The combination of the inserting steps may result in the longitudinal axis of the spacer being perpendicular to the insertion direction. The longitudinal axis of the spacer may be substantially parallel to a medial-lateral axis of the intervertebral disc space. The inserting steps may result in the spacer being positioned in an anterior aspect of the intervertebral disc space. The inserting steps may include allowing the spacer to rotate with respect to the insertion direction. The spacer may further include a front end having frictional properties that are greater than frictional properties of a rear end of the spacer, and the inserting steps may include allowing the front end to turn within the intervertebral disc space as it frictionally engages one or both of the adjacent vertebrae. The on-axis and off-axis interfaces may be ports, the tool may include a retractable member, and the engaging steps may include placing the retractable member in the respective ports. The combination of the inserting steps may result in the longitudinal axis of the spacer being rotated approximately 90 degrees with respect to the insertion direction. The method further includes the step of expanding the spacer. The method may further include the step of packing bone grafting material in one or more openings of the spacer before and/or after expansion has occurred.

The present invention is applicable in any type of spinal surgery. While the focus of the discussion of a preferred embodiment of the invention is directed to lumbar IF surgery, it is to be understood that the invention may be employed in cervical and thoracic spinal procedures as well from any direction, i.e., anterior, posterior and lateral.

The present invention is constructed to decrease patient risk, speed recovery and substantially improve success rates in terms of restoration of normal spinal confirmation and neurological decompression. This is achieved by providing the surgeon with an expandable spacer that is best suited for the patient's condition and alterable in size, dimension and/or shape to further improve the implant's clinical result. These and other advantages of the present invention will become apparent upon review of the following description and accompanying drawings.

DETAILED DESCRIPTION OF THE PREFERRED EMBODIMENTS OF THE INVENTION

Figure 1:
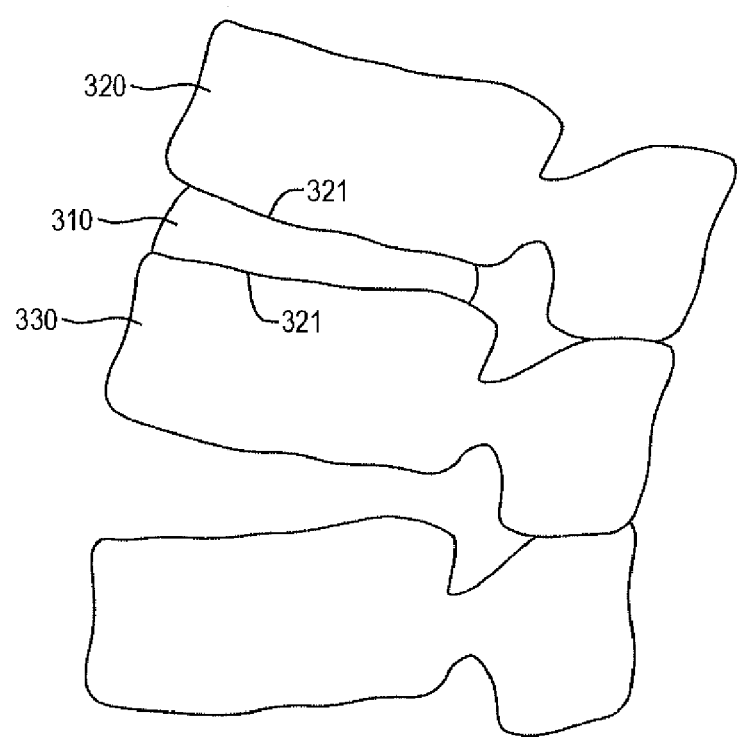
FIG. 1 is a side view representation of a partial spinal arrangement of a vertebral disc and two vertebra, a superior vertebra and an inferior vertebra, that are immediately adjacent to the vertebral disc.
Figure 2:
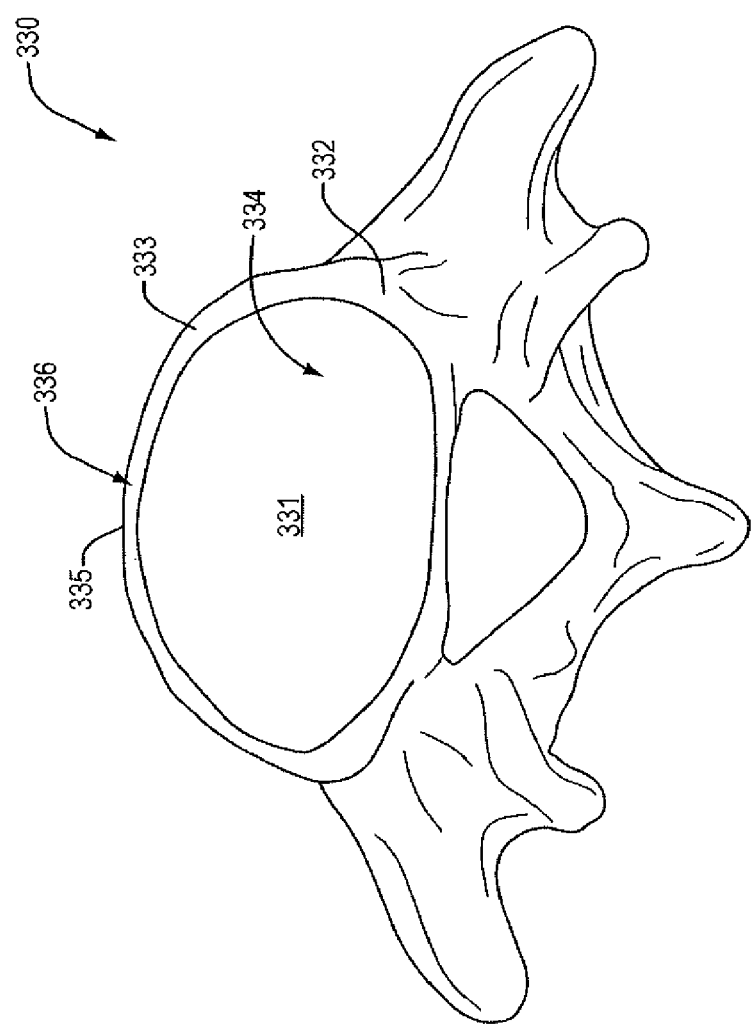
FIG. 2 is a top view of the inferior vertebra of FIG. 1 after the disc of FIG. 1 has been surgically removed from the inferior vertebra.
Figure 3:
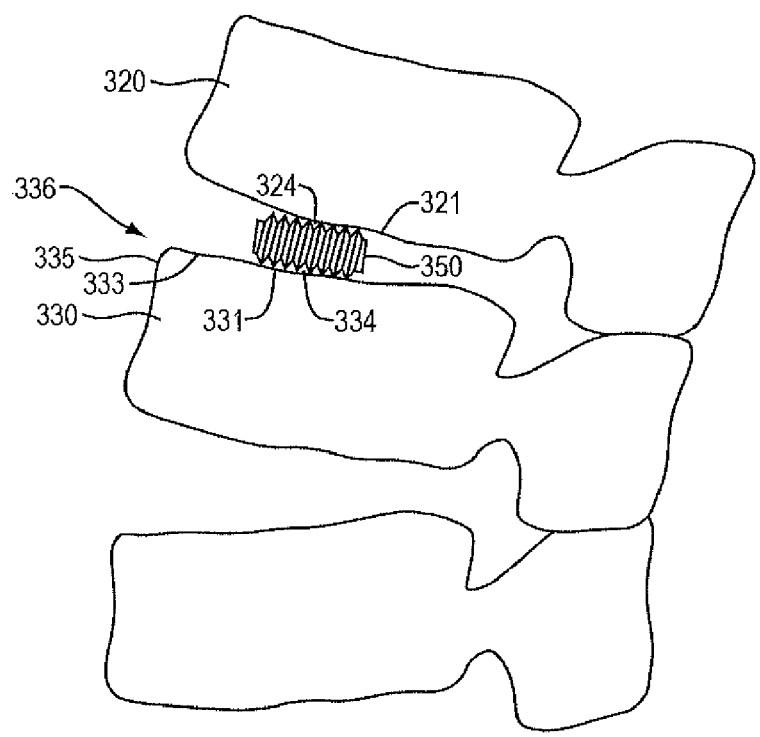
FIG. 3 shows an exemplary prior spinal implant device positioned between the end plate portions of the inferior and superior vertebrae of FIG. 1.
Figure 4:
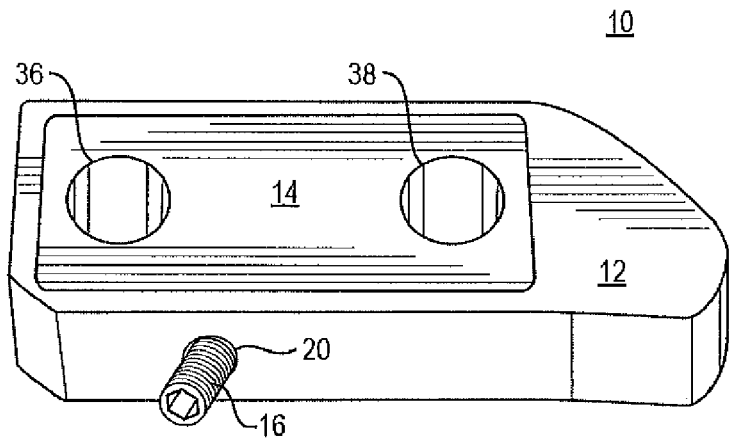
FIG. 4 is a perspective view of a first embodiment of the expandable spacer of the present invention prior to expansion.
Figure 5:
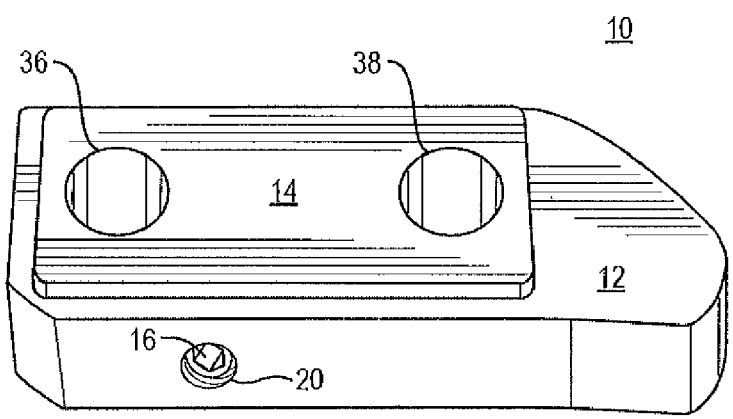
FIG. 5 is a perspective view of the expandable spacer of FIG. 4 in an expanded state.
Figure 6:
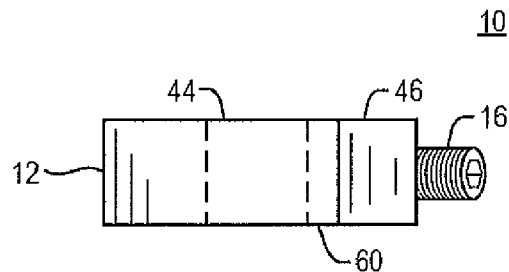
FIG. 6 is a side view of the expandable spacer prior to expansion, corresponding to FIG. 4.
Figure 7:
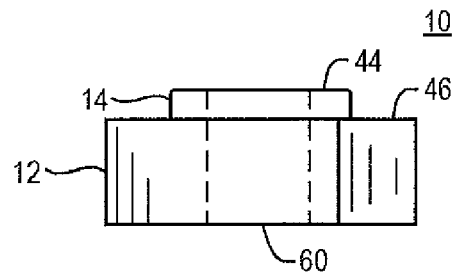
FIG. 7 is a side view of the expandable spacer expanded, corresponding to FIG. 5.
Figure 8:
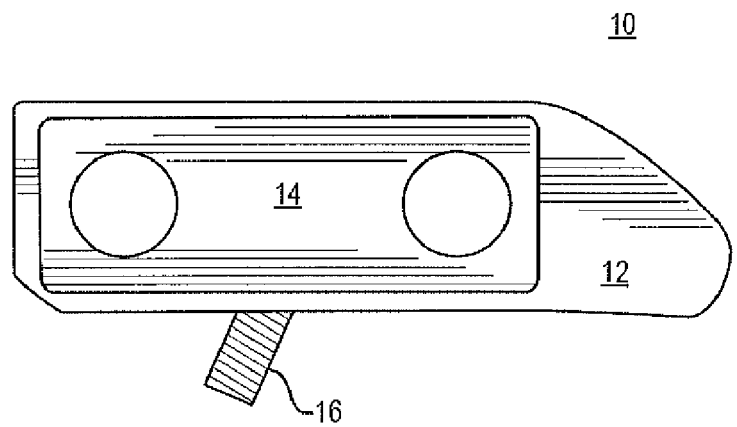
FIG. 8 is a top view of the expandable spacer prior to expansion, corresponding to FIG. 4.
Figure 9:
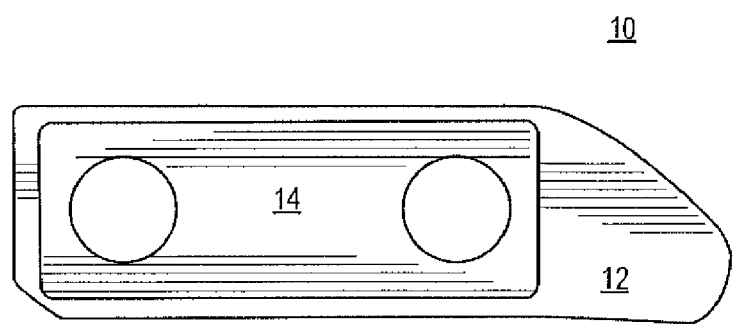
FIG. 9 is a top view of the expandable spacer expanded, corresponding to FIG. 5.

A first embodiment of an expandable spacer 10 of the present invention is shown in FIGS. 4-11. The spacer 10 is shown in FIGS. 4, 6 and 8 prior to expansion, and in FIGS. 5, 7 and 9 in an expanded state. It is to be noted that while the spacer 10 is shown in FIGS. 4-11 in a substantially rectangular shape with a generally curved forward portion, the expandable apparatus of the present invention may come in a range of shapes and sizes. The surgeon may choose a particular spacer size and shape suitable for a given application. The spacer 10 of the present invention is directed to the structural configuration thereof that enables the surgeon to expand the height dimension without any resulting rocking, tilting, slipping, or canting of the spacer 10. The spacer 10 may include one or more on-axis and/or one or more off-axis positioning interface sites. Spacer size, shape and positioning interface site options and examples are described in the present applicant's previously filed provisional application No. 61/040,821 filed Mar. 31, 2008, and provisional application No. 61/091,505 filed Aug. 25, 2008. The contents of those applications are incorporated herein by reference.

The spacer 10 includes a base component 12, a top component 14 and a height adjuster 16. The base component 12 includes a receiver 18 with dimensions and shape suitable to receive and removably retain the top component 14 there. That is, at least a portion of the external dimensions of the top component 14 are less than the internal dimensions of the receiver 18 of the base component 12. In this embodiment the external dimensions of the top component 14 are arranged to fit entirely within the receiver 18. In this embodiment, the receiver 18 of the base component 12 further includes a height adjuster port 20, a height adjuster slot 22 and a plurality of cant minimizing towers such as, for example, first tower 24 and second tower 26. Each tower includes a perimeter wall 28 and may include an interior space 30. The effects of a plurality of silos and towers can be achieved with other configurations of the top and base components of the spacer and are included within the scope of the invention.

In this embodiment, the top component 14 includes a height adjuster port 32, a height adjuster slot 34 and a plurality of cant minimizing silos such as, for example, first silo 36 and second silo 38. Each silo includes a perimeter wall 40 and may include an interior space 42. Each of silos 36 and 38 has dimensions and shape to receive and removably retain therein the towers 24 and 26 of the receiver 18 of the base component 12. That is, the external dimensions of the towers 24 and 26 are less than the internal dimensions of the silos 36 and 38. The base component 12 and the top component 14 as shown in FIGS. 4-11 are arranged so that the top component 14 fits within the receiver 18 of the base component 12, the first tower 24 fits within the first silo 36 and the second tower 26 fits within the second silo 38 when the top component 14 is inserted into the base component 12. In general, outer perimeter 15 of the top component 14 fits within inner perimeter slot 19 of the receiver 18 adjacent to the towers 24 and 26. The base component 12 and the top component 14 are configured so that top surface 44 of the top component 14 is flush with top surface 46 of the base component 12 prior to expansion of the spacer 10, as shown in FIGS. 4 and 6.

The combination of the height adjuster 16, the height adjuster slot 22 of the base component 22 and the height adjuster slot 34 of the top component 14, enables the surgeon to raise the top component 14 with respect to the base component 12, as shown in FIGS. 5 and 7. The height adjuster 16 is sized and shaped with external dimensions that are greater than the internal dimensions of the height adjuster slot 22 of the base component 12 and the height adjuster slot 34 of the top component 14. The height adjuster slots 22 and 34 are inwardly tapered from their respective ports 20 and 32 toward opposing sides 48 and 50. They are also arranged with compatible configurations to form a unitary adjustment channel (not shown) within which the height adjuster 16 may be progressed. As a result, when the top component 14 is positioned in the receiver 18, the height adjuster 16 may be progressed starting from the combination of ports 20 and 32 into the combination of slots 22 and 34 toward opposing sides 48 and 50. As it makes that progression, the height adjuster 16 forces the top component 14 out of the receiver 18 of the base component 12. This arrangement enables the surgeon to increase selectively the height of the spacer 10.

Figure 10:
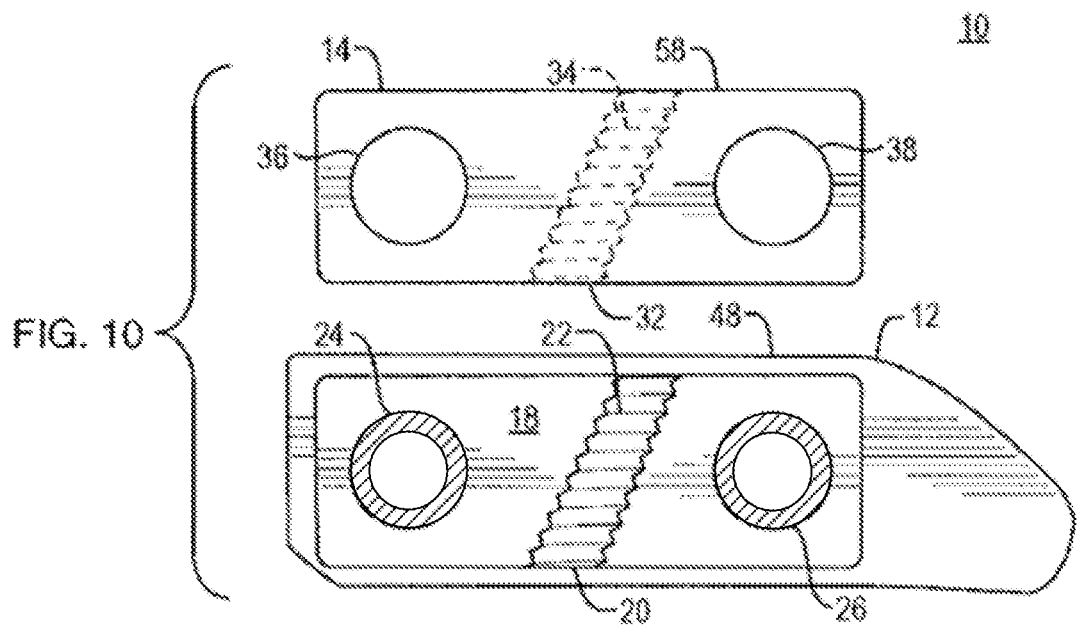
FIG. 10 is a top view of the first embodiment of the expandable spacer with the base component and the top component separated from one another.
Figure 11:
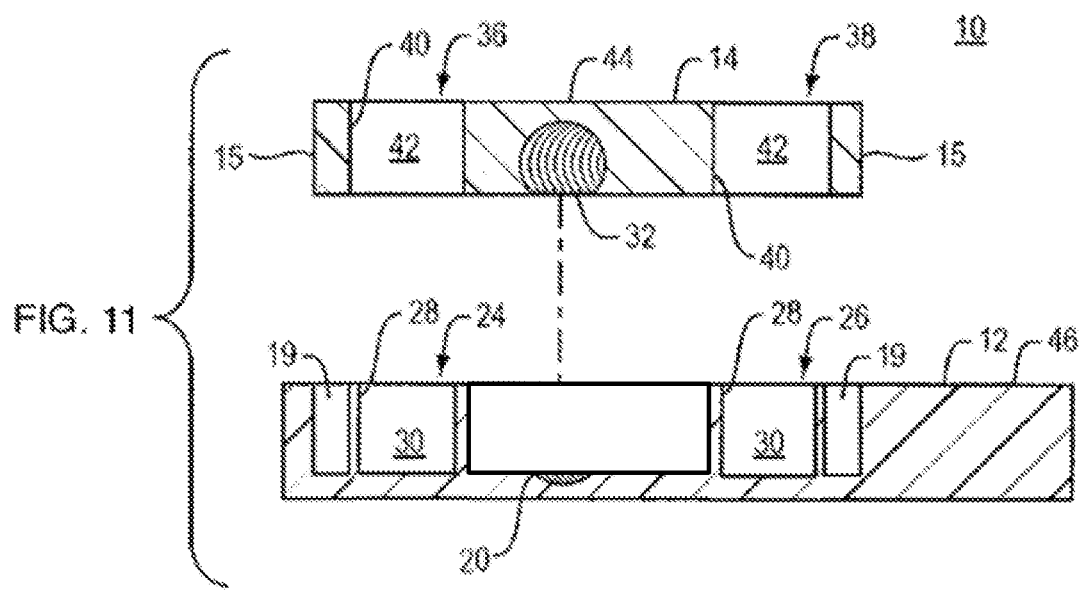
FIG. 11 is a cross sectional side view of the first embodiment of the expandable spacer with the base component and the top component separated from one another.
Figure 12:
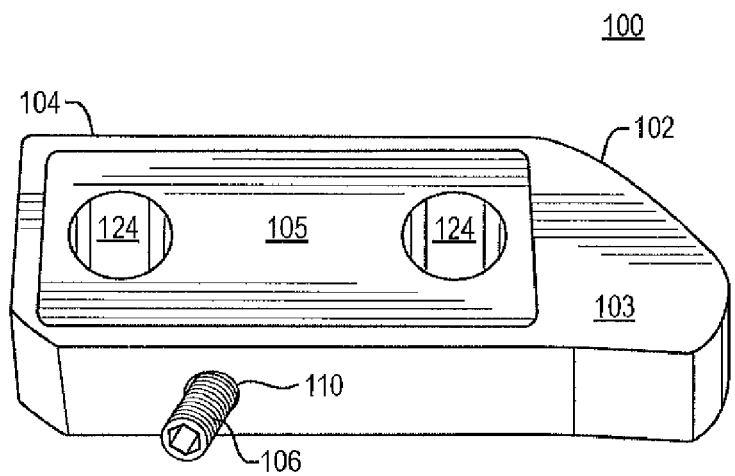
FIG. 12 is a perspective view of a second embodiment of the expandable spacer of the present invention prior to expansion.
Figure 13:
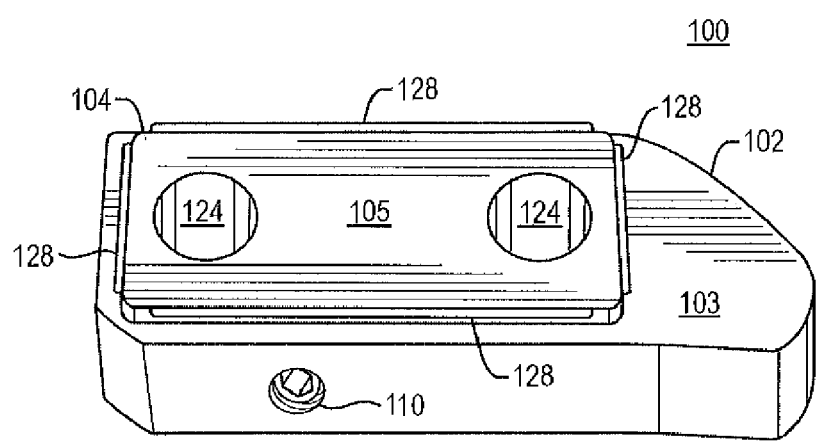
FIG. 13 is a perspective view of the expandable spacer of FIG. 12 in an expanded state.
Figure 14:
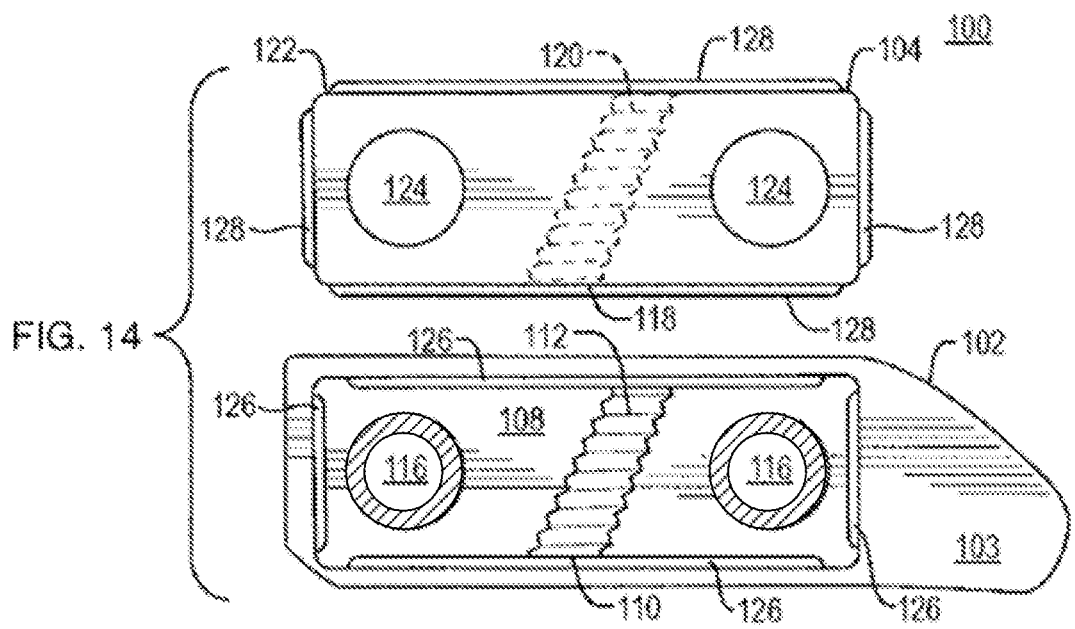
FIG. 14 is a top view of the second embodiment of the expandable spacer with the base component and the top component separated from one another.

The height adjuster 16 may be any means suitable for use in an IF procedure. It must be accessible by the surgeon when the spacer 10 is positioned between vertebrae. When the spacer 10 has been positioned in the location of interest, the height adjuster 16 may be moved into the combination of slots 22 and 34 in a manner that causes the top component 14 to extend upwardly from the base component 12. As shown in FIGS. 10 and 11, the slots 22 and 34 are threaded and tapered. The height adjuster 16 suitable for use with such slot configurations is also threaded but it is not tapered. Instead, it is of fixed diameter so that as it is threaded into the slots 22 and 34, it forces the top component 12 out of the receiver 18. Those of skill in the art will recognize that the height adjuster 16 and the slots 22 and 34 may be of different configurations, provided they are designed to cause the upward movement of the top component 14 with respect to the base component 12 when the height adjuster 16 is moved into the slots 22 and 34.

The height adjuster 16 is an expansion mechanism configured to enable the movement of one component of the spacer 10 with respect to another to cause the expansion/ change in shape of the spacer 10. Other expansion mechanisms may be employed for that purpose without deviating from the scope of the invention. For example, in addition to a screw-type mechanism such as the height adjuster 16 shown in the figures, the expansion mechanism may be a cam, a wedge, or other type of distracting device capable of advancement into the combination of slots 22 and 34 or some other form of port arrangement and capable of displacing the top component 14 with respect to the base component 12, or the base component 12 with respect to the top component 14.

An advantage of the expandable spacer 10 of the present invention is the minimizing of any canting, slipping or tilting during and after expansion. This is achieved by the top and base components remaining in engagement with each other during expansion of the spacer. In this first embodiment this is achieved by the combination of the towers 24 and 26 of the base component 12 and the silos 36 and 38 of the top component 14. In another embodiment, this is achieved by texturing at least a portion of the top and base components that are in contact with each other.

Expandable spacers have been provided in the past; however, as noted, they can be unsuitable for use when the expanded portion extends at an angle so that there is limited contact between the spacer and the vertebra above it. This can cause the patient pain and slow bone growth through the spacer, which can cause delayed recovery for the patient. The spacer 10 eliminates that limitation. When the height adjuster 16 is progressed into the slots 22 and 34, the top component 14 rises uniformly because the top component 14 remains in substantial contact with the base component 12 at the towers/silos interface, or at the textured area of the at least a portion of the top and base components that are in contact with each other. The towers 24/26 and the silos 36/38 or the top and base components, of which at least a portion may be textured, are arranged for close sliding engagement with one another. The tolerance between those structures should be sufficiently close so that there is very little gap between them and, therefore, little or no opportunity for canting, tilting, or unintended slipping to occur.

The spacer 10 further optionally includes means to enable bone growth therethrough to facilitate the fusion process. In one embodiment, each of the towers 24 and 26 of the base component 12 preferably includes interior space 30. Additionally, each of the silos 36 and 38 includes interior space 42. When the base component 12 and the top component 14 are engaged with one another, the interior spaces 30 and 42 are aligned so that there exists a complete passageway from the top surface 44/46 of the spacer 10 to the bottom surface 60. Bone fusion material may be packed into those passageways. That is, more generally, the spacer 10 is configured to include one or more through and through passageways, which passageways allow bone packing in the post-expanded spacer. It is to be noted that the passageways may not be completely through and through. It is also to be noted that the passageways may be filled with the bone grafting material after the spacer 10 has been expanded. In that situation, the passageways may not be completely through and through and/or they may be offset with respect to the top component 14 and the base component 12.

Figure 16:
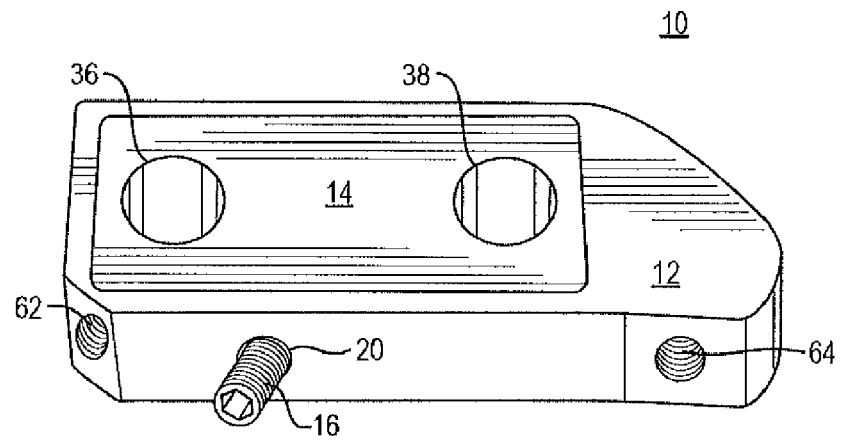
FIG. 16 is a perspective view of an alternative form of the first embodiment of the expandable spacer of the present invention prior to expansion illustrating two off-axis steering interface sites.
Figure 17:
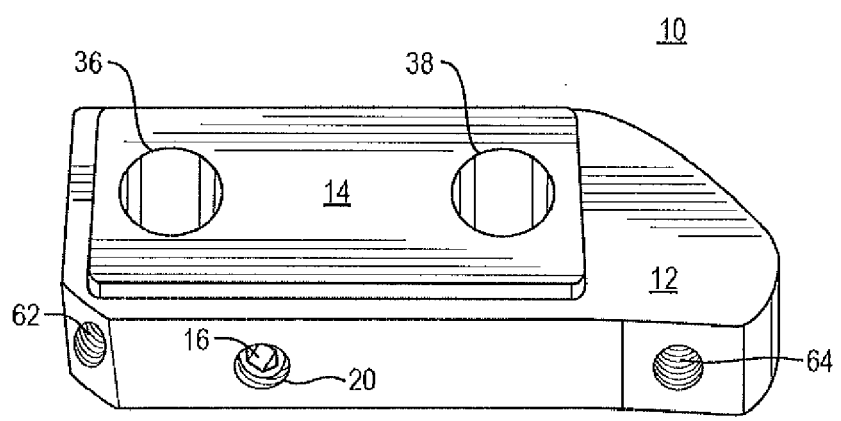
FIG. 17 is a perspective view of the expandable spacer of FIG. 16 in an expanded state.
Figure 18:
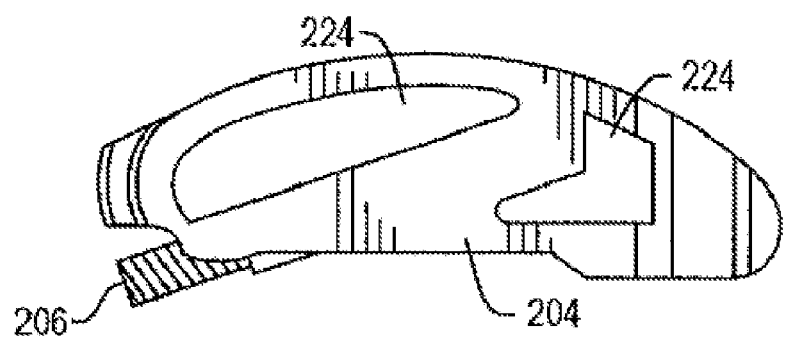
FIG. 18 is a top view of the third embodiment of the expandable spacer of the present invention prior to expansion illustrating two bone packing interior spaces.
Figure 19:
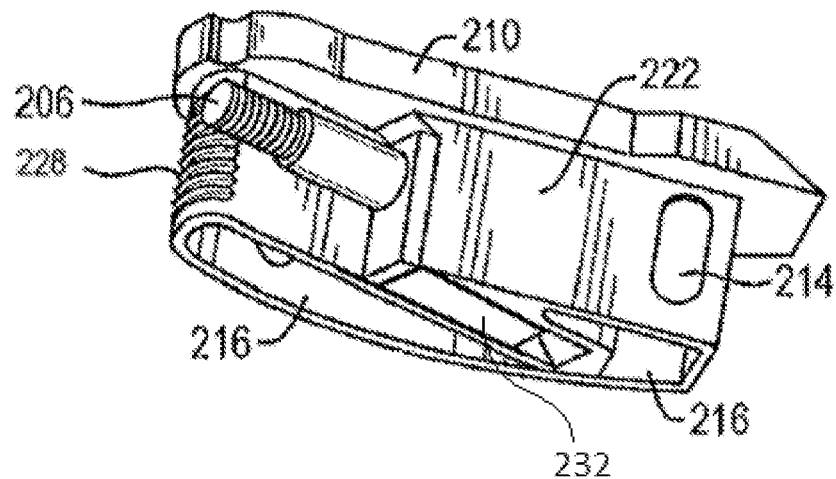
FIG. 19 is a bottom perspective view of the top component of expandable spacer of FIG. 18 illustrating teeth on two portions of the exterior perimeter wall.

The expandable spacer 10 of the present invention may include on-axis and/or off-axis insertion arrangements such as interface ports 62 and 64 as shown in FIGS. 16 and 17. Further, the spacer 10 may be rectangular, curved or other configurations of interest. The spacer may be placed in position using a placement device or tool as described in the other two provisional applications referenced herein, for example.

One or more surfaces of the base component 12 and/or the top component 14 may be textured, sawtoothed, dovetailed and/or otherwise modified to optimize frictional engagement with the vertebrae between which the spacer 10 is positioned to reduce any undesired slipping. The spacer may be configured so that it has a higher frictional engagement at the one end than the other end to enable a desirable type of sliding or positioning of the spacer during insertion.

In addition or alternatively, the portions of the base and top components that are in contact with one another may be textured, sawtoothed, dovetailed, stepped and/or otherwise modified to optimize surface area contact between those components. Doing so reduces any slippage or canting problems associated with the height dimension of the spacer that may occur when the spacer is an expanded state, including when expanded in the desired intervertebral position.

A second embodiment of an expandable spacer 100 depicting this configuration is shown in FIGS. 12-15, wherein elements corresponding to like elements of the expandable spacer 10 have the same identifying numbers. The expandable spacer 100 includes a base component 102, a top component 104 and a height adjuster 106. The base component 102 includes a receiver 108 with dimensions and shape suitable to receive and removably retain the top component 104 there. That is, the external dimensions of the top component 104 are less than the internal dimensions of the receiver 108 of the base component 102. The receiver 108 of the base component 102 further includes a height adjuster port 110, a height adjuster slot 112 and an interior perimeter wall 114. The base component 102 also includes one or more base packing ports 116 extending entirely therethrough at least in the receiver 108 area but not limited thereto. The base component 102 and the top component 104 are configured so that top surface 105 of the top component 104 is flush with top surface 103 of the base component 102 prior to expansion of the spacer 100. The expandable spacer 100 may be expanded in the manner described with respect to the spacer 10.

The top component 104 includes a height adjuster port 118, a height adjuster slot 120 and an exterior perimeter wall 122. The top component 104 also includes one or more top packing ports 124 extending entirely therethrough and configured to align with the one or more base packing ports 116 so that when the base component 102 and the top component 104 are engaged with one another, there is at least one port extending entirely through the spacer 100 to permit bone packing therein. It is to be understood that the bone packing ports can be arranged in other configurations and remain within the scope of the invention. The dimensions of the top component 104 are selected to ensure that the top component fits snugly within the receiver 108 of the base component 102. It is to be noted that the bone packing ports may be employed to pack bone grafting material after the spacer 100 has been expanded. In that situation, passageways from one side of the spacer 100 to the other may not be completely direct but may have one or more offset aspects.

Figure 15:
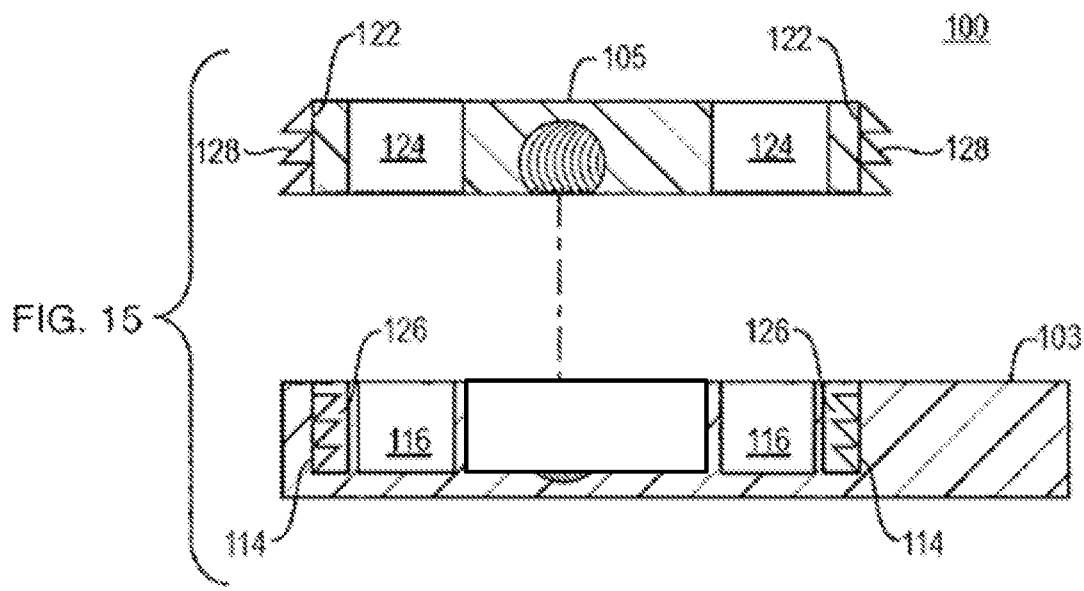
FIG. 15 is a cross sectional side view of the expandable spacer of FIG. 12, showing internal surface modifications to promote surface area contact between the base and top components.

The interior perimeter wall 114 of the base component 102 and the exterior perimeter wall 122 of the top component 104 are configured to increase the surface contact area between those two components and are textured, sawtoothed, dovetailed and/or otherwise modified to optimize frictional engagement with these components to reduce any undesired tilting, canting, or slipping during and after expansion of the spacer 100. The modification may be located on the entirety of the component surfaces in engagement with each other or a portion thereof. For example, the modification may be located at the opposite ends of the longitudinal axis of the spacer. In the embodiment depicted, the entirety of the interior perimeter wall 114 and the exterior perimeter wall 122 are not smooth. In this embodiment of the expandable spacer 100, the interior perimeter wall 114 of the base component 102 includes a plurality of tiers of interior steps 126 and the exterior perimeter wall 122 of the top component 104 includes a plurality of tiers of exterior steps 128. The interior steps 126 and the exterior steps 128 are configured in mirror opposing orientations so that when the spacer 100 is expanded, the steps 126/128 interlock with one another, thereby increasing the engagement of the top component 104 with the base component 102 so that the two remain in secure contact with one another, minimizing any height slippage or canting of the spacer 100 when in an expanded state. As shown in FIG. 15, and beginning from top surface 103 of the base component 102, the steps 126 of the base component 102 extend outward horizontally from the interior perimeter wall 114 and angle downward and inward back to the interior perimeter wall 114. Further, beginning from top surface 105 of the top component 104, the steps 128 extend outward and downward at an angle from the exterior perimeter wall 122 before extending rearward horizontally back to the exterior perimeter wall 122. The angles of the steps 126 and 128 should be substantially equal and opposite. Those of skill in the art will recognize that other interlocking configurations of the steps 126 and 128 may be established.

The steps 126/128 may be of sawtooth configuration as shown, or they may be rectangular, triangular or other suitable configuration. The steps 126/128 may be located on all component surfaces or portions thereof. In alternative embodiments of the expandable spacer 100, the interior perimeter walls 114 of the base component 102 and the exterior perimeter walls 122 of the top component 104 may be textured, dovetailed or otherwise surface modified to enhance the frictional engagement therebetween. The step arrangement provides a ratcheting or ladder-like mechanism to enable expansion while eliminating or minimizing toggling or settling of the spacer 100.

The steps 126 and 128 of the expandable spacer 100 may be elastically deformable in one direction so that when the spacer 100 is expanded, the steps 126 of the base component 102 may give as the steps 128 of the top component 104 are pushed pass them with the insertion of the height adjuster 16 into slots 20 and 32. Once a set of steps 128 of a particular tier engages a set of steps 126 of a tier above, there is resistance to a return of that set of steps 128 to a lower tier of the set of base component steps 126. Further, the spacing between tiers of steps 126/128 may be established in specific increments so that the surgeon is able to adjust the height increase of the spacer 100 very specifically by counting the number of tiers of step engagement that occurs. For example, each tier may be spaced from adjacent tiers by one millimeter. Making three incremental changes in stepped tier engagements would correspond to a three millimeter spacer expansion.

Relatedly, the height adjuster 106 may be arranged with coding such that its rotation by some selected value corresponds to a tier change. I.e., a quarter-turn culminating with a click can be used to signify that a tier change has been made. Those of skill in the art will recognize that other arrangements for linking height adjuster changes with expansion values may be established without deviating from this concept.

The embodiment of the expandable spacer 100 shown in FIGS. 12-15 has no cant-minimizing silos and towers arrangement such as included in the spacer 10 of FIGS. 4-11. Nevertheless, the spacer 100 may optionally include such silo-and-tower arrangement. If the silos and towers are included, they may or may not also include steps corresponding to the steps 126/128 of the perimeter walls of the base component 102 and the top component 104.

Although not depicted in this embodiment, the spacer 100 can be made with steering ports or interface sites to enable a surgeon to position the spacer in a desired position. The expandable spacer 100 of the present invention may include on-axis and/or off-axis insertion arrangements or ports as shown in FIGS. 16 and 17 in relation to spacer 10. Further, the spacer 100 may be rectangular, curved or other configurations of interest. The spacer may be placed in position using a placement device or tool as described in the other two provisional applications listed herein.

A third embodiment of an expandable spacer 200 is shown in FIGS. 18-23, wherein elements corresponding to like elements of the expandable spacer 10 have the same identifying numbers. The expandable spacer 200 includes a base component 202, a top component 204 and a height adjuster 206. The base component 202 includes a receiver 208 with dimensions and shape suitable to receive and removably retain a portion of the top component 204 there. That is, a portion of the external dimensions of the top component 204 are less than the internal dimensions of the receiver 208 of the base component 202. The top component 204 has a cap 210 that does not fit within the internal dimensions of the receiver 208 (see FIG. 19), and extends over the base component 202. The cap 210 of the top component 204 ends in two beveled surfaces on the opposite end of the spacer 200 from the height adjuster 206. In this embodiment the cap 210 sits on top of the base component 202 over the entire perimeter thereof. However, it is to be understood that other configurations or arrangements of a top component 204 with a cap 210 or partial cap (not shown) are within the scope of the invention. The base component 202 includes bone packing ports 212 on the side wall of the base component 202, and also includes one or more bone packing ports 216 extending entirely therethrough at least in the receiver 208 area. Other bone packing port arrangements or configurations are encompassed in the invention. It is to be noted that the bone packing ports may be employed to pack bone grafting material after the spacer 200 has been expanded. In that situation, passageways from one side of the spacer 200 to the other may not be completely direct but may have one or more offset aspects.

Figure 20:
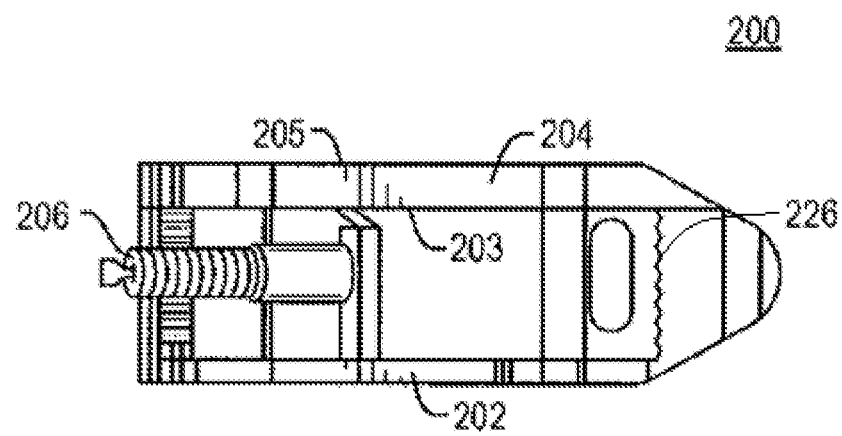
FIG. 20 is a side view of the third embodiment of the expandable spacer of the present invention prior to expansion.
Figure 21:
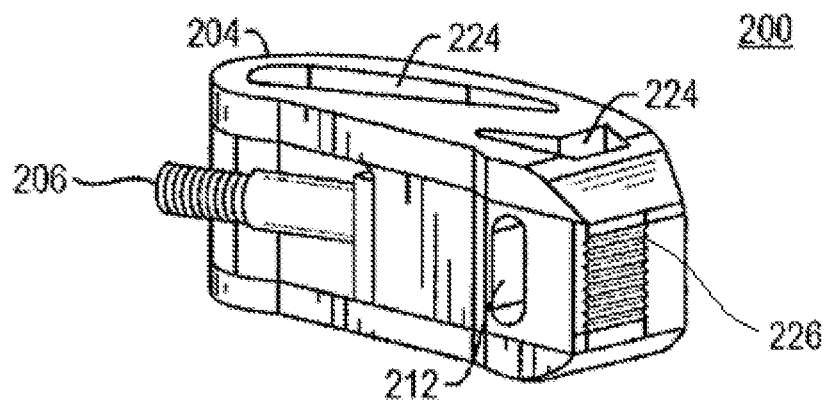
FIG. 21 is a perspective view of the expandable spacer of FIG. 20 prior to expansion.
Figure 22:
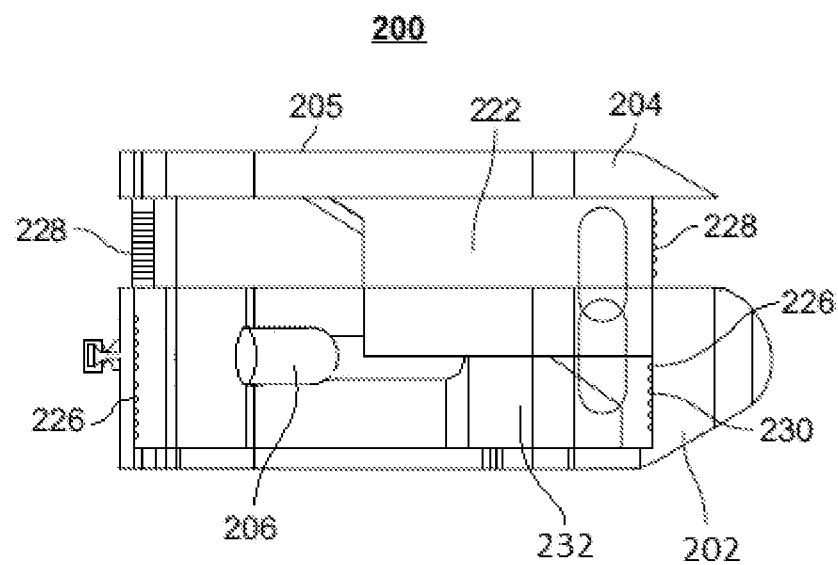
FIG. 22 is side view of the third embodiment of the expandable spacer of the present invention in an expanded state, illustrating the interlocking teeth engaging two portions of the top and base components.

As shown in FIGS. 20 and 21, the base component 202 and the top component 204 are configured so that the bottom of the top surface 205 of the top component 204 sits directly on the top surface 203 of the base component 202 prior to expansion of the spacer 200. The expandable spacer 200 may be expanded in the manner described with respect to the spacer 10. In this embodiment, the height adjuster 206 is a screw-type mechanism situated at one end of the spacer at an angle to the longitudinal axis of the spacer that pushes against a lifting wedge 232, which causes the top component 204 to rise from the base component 202. As a result, when the top component 204 is positioned in the receiver 208, the height adjuster 206 may be progressed from where it extends beyond the perimeter wall of the top component 204 and base component 202, pushing the lifting wedge 232 towards the same end of the spacer as the beveled end of the cap 210.

The top component 204 includes bone packing ports 214 on the side wall of the top component 204, and also includes one or more top packing ports 224 extending entirely therethrough and configured to align with the one or more base packing ports 216 so that when the base component 202 and the top component 204 are engaged with one another, there is at least one port extending entirely through the spacer 200 to permit bone packing therein. It is to be understood that the bone packing ports can be arranged in other configurations and remain within the scope of the invention. The dimensions of the top component 204 are selected to ensure that the top component fits snugly within the receiver 208 of the base component 202.

An interior perimeter wall 230 of the base component 202 and an exterior perimeter wall 222 of the top component 204 are configured to increase the surface contact area between those two components and are textured, sawtoothed, dovetailed and/or otherwise modified to optimize frictional engagement with these components to reduce any undesired tilting, canting, or slipping during and after expansion of the spacer 200. The modification may be located on the entirety of the component surfaces in engagement with each other or a portion thereof. For example, the modification may be located at the opposite ends of the longitudinal axis of the spacer 200. In the embodiment depicted, the modification is located at two discrete locations at opposite ends of the longitudinal axis of the spacer 200. That is, a portion the interior perimeter wall 230 and the exterior perimeter wall 222 are textured. In this embodiment of the expandable spacer 200, the interior perimeter wall 230 of the base component 202 includes directional locking teeth 226 and the exterior perimeter wall 222 of the top component 204 includes complimentary teeth 228 (see FIG. 22). The interior teeth 226 and the exterior teeth 228 are configured in mirror opposing orientations so that when the spacer 200 is expanded, the teeth 226/228 interlock with one another, thereby increasing the engagement of the top component 204 with the base component 202 so that the two remain in secure contact with one another, minimizing any height slippage or canting of the spacer 200 during expansion or when in an expanded state. It is to be noted that a portion or all of the interior perimeter wall 230 and a portion or all of the exterior perimeter wall 222 may be textured.

Figure 23:
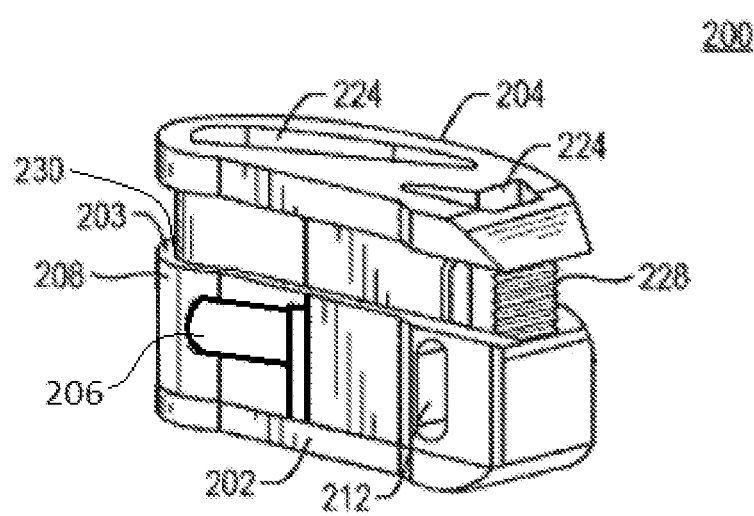
FIG. 23 is a perspective view of the expandable spacer of FIG. 22 in an expanded state.

As shown in FIG. 23, and beginning from top surface 203 of the base component 202, the teeth 226 of the base component 202 extend outward horizontally from the interior perimeter wall 230 and angle downward and inward back to the interior perimeter wall 214. Further, beginning from top surface 205 of the top component 204, the teeth 228 extend outward and downward at an angle from the exterior perimeter wall 222 before extending rearward horizontally back to the exterior perimeter wall 222. The angles of the teeth 226 and 228 should be substantially equal and opposite. Those of skill in the art will recognize that other interlocking configurations of the teeth 226 and 228 may be established and are within the scope of the invention.

The teeth 226/228 may be of sawtooth configuration as shown, or they may be rectangular, triangular or other suitable configuration. The teeth 226/228 may be located on all component surfaces or portions thereof. In alternative embodiments of the expandable spacer 200 the interior perimeter wall 230 of the base component 202 and the exterior perimeter wall 222 of the top component 204 may be textured, dovetailed or otherwise surface modified to enhance the frictional engagement therebetween. The teeth arrangement provides a ratcheting or ladder-like mechanism to enable expansion while eliminating or minimizing canting, tilting, or settling of the spacer 200.

The teeth 226 and 228 of the expandable spacer 200 may be elastically deformable in one direction so that when the spacer 200 is expanded, the teeth 226 of the base component 202 may give as the teeth 228 of the top component 204 are pushed past them. Once a set of teeth 228 engages the teeth 226 of a tier above, there is resistance to a return of that set of teeth 228 to a lower tier of the set of base component teeth 226. Further, the spacing between tiers of teeth 226/228 may be established in specific increments so that the surgeon is able to adjust the height increase of the spacer 200 very specifically by counting the number of tiers of engagement of the teeth that occurs. For example, each tier may be spaced from adjacent tiers by one millimeter. Making three incremental changes in stepped tier engagements would correspond to a three millimeter spacer expansion.

Relatedly, the height adjuster 206 may be arranged with coding such that its rotation by some selected value corresponds to a tier change. i.e., a quarter-turn culminating with a click can be used to signify that a tier change has been made. Those of skill in the art will recognize that other arrangements for linking height adjuster changes with expansion values may be established without deviating from this concept.

The configuration of the expandable spacer 200 shown in FIGS. 18-23 has no cant-minimizing silos and towers arrangement such as included in the spacer 10 of FIGS. 4-11. Nevertheless, the spacer 200 may optionally include such silo-and-tower arrangement. If the silos and towers are included, they may or may not also include teeth corresponding to the teeth 226/228 of the perimeter walls of the base component 202 and the top component 204.

Although not depicted in this embodiment, the spacer 200 can be made with steering ports or interface sites to enable a surgeon to position the spacer in a desired position. The expandable spacer 200 of the present invention may include on-axis and/or off-axis insertion arrangements or ports as shown in FIGS. 16 and 17 in relation to spacer 10. Further, the spacer 200 may be rectangular, curved or other configurations of interest. The spacer may be placed in position using a placement device or tool as described in the other two provisional applications listed herein.

The present invention also encompasses a method of inserting and positioning the expandable spacers described above into the intervertebral disc space between two adjacent vertebrae comprising the steps of providing an expandable spacer including a top component, a base component in engagement with the top component, and an expansion mechanism arranged to change the top component's position with respect to the base component. The spacer may include one or more off-axis positioning interface sites and/or one or more on-axis positioning sites, the on-axis interface being coincident with or parallel to the longitudinal axis of the spacer, and the off-axis interface being angled with respect to the longitudinal axis. The method may comprise the steps of engaging a tool to the on-axis interface if present, inserting the spacer at least partially into the intervertebral disc space by moving the tool substantially along an insertion direction, engaging the tool to the off-axis interface if present, and inserting the spacer further into the intervertebral disc space by moving the tool substantially along the insertion direction, such that the longitudinal axis of the spacer is angled with respect to the insertion direction. The method may further include the steps of engaging the tool to a second off-axis interface of the spacer if present, and inserting the spacer further into the intervertebral disc space by moving the tool substantially along the insertion direction. The spacer may further include a front end having frictional properties that are greater than frictional properties of a rear end of the spacer, and the inserting steps may include allowing the front end to turn within the intervertebral disc space as it frictionally engages one or both of the adjacent vertebrae. The method may further include the step of packing bone grafting material into at least one of the on-axis interface, the off-axis interface, and an opening in the spacer. The method further includes the step of expanding the spacer. The method further includes the optional step of packing bone grafting material into one or more ports of the spacer after expansion has occurred.

The expandable spacers 10, 100, and 200 of the present invention have been described with respect to three specific embodiments and methods of using the same. Nevertheless, it is to be understood that various modifications may be made without departing from the spirit and scope of the invention. All equivalents are deemed to fall within the scope of these descriptions of the invention.

The invention claimed is:

1. A method of implanting a spinal spacer into an intervertebral space of a patient, comprising:
   engaging a tip of an insertion tool to the spacer so that the insertion tool is substantially parallel to a longitudinal axis of the spacer;
   inserting a front end of the spacer into the intervertebral space along an insertion direction substantially parallel to the longitudinal axis of the spacer while the spacer is in an unexpanded condition; and
   while the spacer is positioned in the intervertebral space, actuating an expansion mechanism to expand the spacer into an expanded condition by increasing a distance between a top component of the spacer and a base component of the spacer, the top component having a cap, a leading end, and a trailing end, the base component having a leading end, a trailing end, and a receiver extending along the longitudinal axis of the spacer, the receiver sized and shaped to receive and movably retain a portion of the top component therein,
   wherein actuating the expansion mechanism includes rotating the expansion mechanism to drive a wedge toward the leading end of the top component,
   wherein the spacer includes an internally threaded interface in the receiver aligned with the longitudinal axis of the spacer and configured to receive the insertion tool therein.

2. The method of claim 1, wherein the expansion mechanism has external threads and extends into the trailing end of the base component.

3. The method of claim 2, wherein while the spacer is in the intervertebral space in the unexpanded condition, the cap is flush with the receiver.

4. The method of claim 3, wherein driving the wedge toward the leading end of the top component transitions the spacer from the unexpanded condition to the expanded condition in which the cap is spaced away from the receiver.

5. The method of claim 1, wherein the expansion mechanism extends at an oblique angle relative to the longitudinal axis of the spacer.

6. The method of claim 1, wherein actuating the expansion mechanism to expand the spacer is performed such that the top component of the spacer does not tilt with respect to the base component of the spacer.

7. The method of claim 6, wherein actuating the expansion mechanism to expand the spacer includes driving the top component of the spacer away from the base component of the spacer, the top component of the spacer remaining in contact with the base component of the spacer during actuation.

8. The method of claim 1, wherein the top component includes a textured exterior wall.

9. The method of claim 1, wherein in the unexpanded condition, a top surface of the top component is parallel to a bottom surface of the bottom component.

10. A method of implanting a spinal spacer into an intervertebral space of a patient, comprising:
   threading a tip of an insertion tool to the spacer so that the insertion tool is substantially parallel to a longitudinal axis of the spacer;
   inserting a front end of the spacer into the intervertebral space along an insertion direction substantially parallel to the longitudinal axis of the spacer while the spacer is in an unexpanded condition; and
   while the spacer is positioned in the intervertebral space, actuating an expansion mechanism to expand the spacer into an expanded condition by increasing a distance between a top component of the spacer and a base component of the spacer, the top component having a cap, a leading end, and a trailing end, the base component having a leading end, a trailing end, and a receiver extending along the longitudinal axis of the spacer, the receiver sized and shaped to receive and movably retain a portion of the top component therein,
   wherein actuating the expansion mechanism includes rotating the expansion mechanism to drive a wedge toward the leading end of the top component,
   wherein the leading end of the top component has a bevel, the leading end of the base component has a tapered portion that is integral with the base component and that decreases in height toward the leading end of the base component, and in the unexpanded condition, the bevel of the leading end of the top component and the tapered portion of the leading end of the base component are substantially continuous with each other.

11. A method of implanting a spinal spacer into an intervertebral space of a patient, comprising:
   threading a tip of an insertion tool to the spacer so that the insertion tool is substantially parallel to a longitudinal axis of the spacer;
   inserting a front end of the spacer into the intervertebral space along an insertion direction substantially parallel to the longitudinal axis of the spacer while the spacer is in an unexpanded condition; and
   while the spacer is positioned in the intervertebral space, actuating an expansion mechanism to expand the spacer into an expanded condition by increasing a distance between a top component of the spacer and a base component of the spacer, the top component having a cap, a leading end, and a trailing end, the base component having a leading end, a trailing end, a side wall extending between the leading end and the trailing end of the base component, and a receiver extending along the longitudinal axis of the spacer, the receiver sized and shaped to receive and movably retain a portion of the top component therein,
   wherein actuating the expansion mechanism includes rotating the expansion mechanism to drive a wedge toward the leading end of the top component,
   wherein the top component includes a first port extending entirely through the top component; and
   at least partially filling the first port with bone grafting material by inserting the bone grafting material into a graft window in the side wall of the base of the spacer after actuating the expansion mechanism to expand the spacer.

12. The method of claim 11, wherein the base component includes a second port extending entirely through the base component.

13. The method of claim 12, wherein the first port aligns with the second port.

* * * * *